(12) United States Patent
Haeffelin et al.

(10) Patent No.: US 10,281,358 B2
(45) Date of Patent: May 7, 2019

(54) SEMICONDUCTOR SENSOR FOR GAS CONCENTRATION

(71) Applicant: Robert Bosch GmbH, Stuttgart (DE)

(72) Inventors: Andreas Haeffelin, Vaihingen (DE);
Harald Guenschel, Gerach (DE);
Janine Riedrich-Moeller, Weil Der Stadt (DE); Marcus Ahles, Pfullingen (DE)

(73) Assignee: ROBERT BOSCH GMBH, Stuttgart (DE)

(*) Notice: Subject to any disclaimer, the term of this patent is extended or adjusted under 35 U.S.C. 154(b) by 304 days.

(21) Appl. No.: 15/416,406

(22) Filed: Jan. 26, 2017

(65) Prior Publication Data
US 2017/0212009 A1    Jul. 27, 2017

(30) Foreign Application Priority Data
Jan. 27, 2016    (DE) .................. 10 2016 201 144

(51) Int. Cl.
| | | |
|---|---|---|
| *G01N 33/00* | (2006.01) | |
| *G01M 15/10* | (2006.01) | |
| *G01N 27/407* | (2006.01) | |
| *G01N 27/41* | (2006.01) | |
| *G01N 27/419* | (2006.01) | |

(52) U.S. Cl.
CPC ........ *G01M 15/104* (2013.01); *G01N 27/407* (2013.01); *G01N 27/4071* (2013.01); *G01N 27/41* (2013.01); *G01N 27/419* (2013.01); *G01N 33/0036* (2013.01); *G01N 33/0037* (2013.01)

(58) Field of Classification Search
CPC .......... G01M 15/104; G01N 33/0036; G01N 33/0037; G01N 27/419; G01N 27/407; G01N 27/4071; G01N 27/41
See application file for complete search history.

(56) References Cited

U.S. PATENT DOCUMENTS

| | | | | |
|---|---|---|---|---|
| 8,506,780 B2* | 8/2013 | Murakami | ........... | G01N 27/419 204/421 |
| 2004/0138825 A1* | 7/2004 | Kawase | ............... | G01N 27/419 702/24 |
| 2010/0126883 A1* | 5/2010 | Runge | .................. | G01N 27/419 205/784.5 |

FOREIGN PATENT DOCUMENTS

| | | |
|---|---|---|
| DE | 102004036032 A1 | 7/2005 |
| DE | 102004036035 A1 | 7/2005 |
| WO | 0202458 A1 | 1/2002 |

* cited by examiner

*Primary Examiner* — Blake A Tankersley
(74) *Attorney, Agent, or Firm* — Norton Rose Fulbright US LLP; Gerard Messina

(57) ABSTRACT

A semiconductor sensor includes a cavity; a fluid connection between the cavity and an inlet area; a pump diaphragm that bounds the cavity; and a measuring diaphragm that bounds the cavity. The fluid connection includes a diffusion channel having multiple openings in the inlet area or multiple diffusion channels having respectively an opening in the inlet area, and it is possible to close at least one of the openings using laser light in order to influence an effective length or an effective cross section of the fluid connection.

9 Claims, 2 Drawing Sheets

SEMICONDUCTOR SENSOR FOR GAS CONCENTRATION

RELATED APPLICATION INFORMATION

The present application claims priority to and the benefit of German patent application no. 10 2016 201 144.8, which was filed in Germany on Jan. 27, 2016, the disclosure of which is incorporated herein by reference.

FIELD OF THE INVENTION

The present invention relates to a sensor for a gas concentration. The present invention in particular relates to a sensor on a semiconductor basis.

BACKGROUND INFORMATION

It is possible to use a lambda probe in order to assess the combustion in an internal combustion engine with respect to a composition of a fuel-air mixture. The lambda probe includes a Nernst cell for determining a difference in the concentration of oxygen between two different gases, namely, the exhaust gas and usually an ambient air. A broadband lambda probe includes a cavity, a pump diaphragm and a measuring diaphragm. The pump diaphragm is controlled so as to convey exhaust gas through a fluid connection into the cavity or out of the cavity so that the tension on the measuring diaphragm, which practically represents a Nernst cell, has a predetermined value. It is then possible to determine the concentration of oxygen in the exhaust gas on the basis of the pump current. In another specific embodiment, it is possible to determine indirectly a concentration of nitrogen oxides in the exhaust gas in that the nitrogen oxides from the exhaust gas are catalytically split and the oxygen arising in the process is determined using another measuring diaphragm.

In order to establish a predetermined correlation between the pump current and a concentration of oxygen in the exhaust gas, normally each individually produced sensor must be adjusted individually. In one specific embodiment, the sensor is disposed on a ceramics substrate, it being possible to produce cuts in the surface of the ceramics using laser light in order to shorten the fluid connection and thus to reduce a flow resistance.

SUMMARY OF THE INVENTION

It is desirable to construct such a sensor in semiconductor technology. The present invention is based on the objective of providing an adjustable semiconductor sensor for gas analysis as well as a method for adjusting the semiconductor sensor. The present invention achieves this objective by way of the subject matters of the independent claims. The further descriptions represent specific embodiments.

A semiconductor sensor includes a cavity, a fluid connection between the cavity and an inlet area, a pump diaphragm that bounds the cavity and a measuring diaphragm that bounds the cavity. The fluid connection includes a diffusion channel having multiple openings in the inlet area or multiple diffusion channels having respectively one opening in the inlet area. At least one of the openings may be closed using laser light in order to influence an effective length or an effective cross section of the fluid connection.

By selectively closing one or more openings, it is possible to adjust the fluid connection in order to adjust a ready-made semiconductor sensor individually. Thus it is possible to provide in particular a sensor for gas analysis, namely, for determining a residual oxygen content in an exhaust gas of an internal combustion engine, which may be constructed using semiconductor technology and may be adjusted in a relatively simple manner. It is thereby possible to produce the diffusion channel in a precise geometry.

It particularly may be that the fluid connection and the cavity be developed in their own semiconductor material. The development of cavities in semiconductor material may occur in particular using the APSM process that is discussed in more detail for example in WO 02/02458, DE 10 2004 036 032 A1 or DE 10 2004 036 035 A1.

It particularly may be that a material is applied in the area of the opening that absorbs infrared radiation to a greater degree that does the semiconductor material such that the material may be molten by an infrared laser in order to close the opening. The semiconductor material may include silicon for example, which is essentially transmissive to infrared radiation. The material in the area of the opening may include silicon nitride for example, for instance $Si_3N_4$. The material may either melt itself and close the opening or it may promote the melting of the semiconductor material such that the latter closes the opening. Silicon nitride sublimates at approx. 1900° C. such that it may be used for promoting the melting of the semiconductor material.

In one specific embodiment, multiple diffusion channels are provided that have varying effective cross sections. By selecting a diffusion channel or by a fluid parallel connection of multiple diffusion channels, it is possible to adapt the flow properties of the fluid connection within broad limits. In another specific embodiment, it is also possible to provide a meander-shaped diffusion channel.

In a specific embodiment, the cavity is formed between a first and a second semiconductor substrate, which are connected to each other. The cavity and possibly also the fluid connection may be produced easily in that a recess is introduced into one of the semiconductor substrates which is closed by the other semiconductor substrate.

In another specific embodiment, a second cavity is provided, which is connected by another fluid connection to the first cavity and is bounded by a second measuring diaphragm. The second measuring diaphragm may be used in particular for the indirect determination of nitrogen oxides in the exhaust gas. The additional fluid connection may be produced like the first one. Optionally, the second fluid connection may also be adjusted by closing openings in diffusion channels.

A method for producing a semiconductor sensor includes steps of providing the above-described semiconductor sensor, of providing a gas having a known composition in the area of the inlet, of controlling the pump diaphragm in such a way that a predetermined tension sets in on the measuring diaphragm, and of closing one or multiple openings as a function of a pump current flowing through the pump diaphragm in order to establish a predetermined correlation between the pump current and the composition of the gas.

In this manner, it is possible individually to calibrate the ready-made semiconductor sensor. Laser light may be used in a facility as is currently used for introducing cuts in ceramic material.

The present invention will now be described in more detail with reference to the accompanying figures.

DETAILED DESCRIPTION

Figure 1:
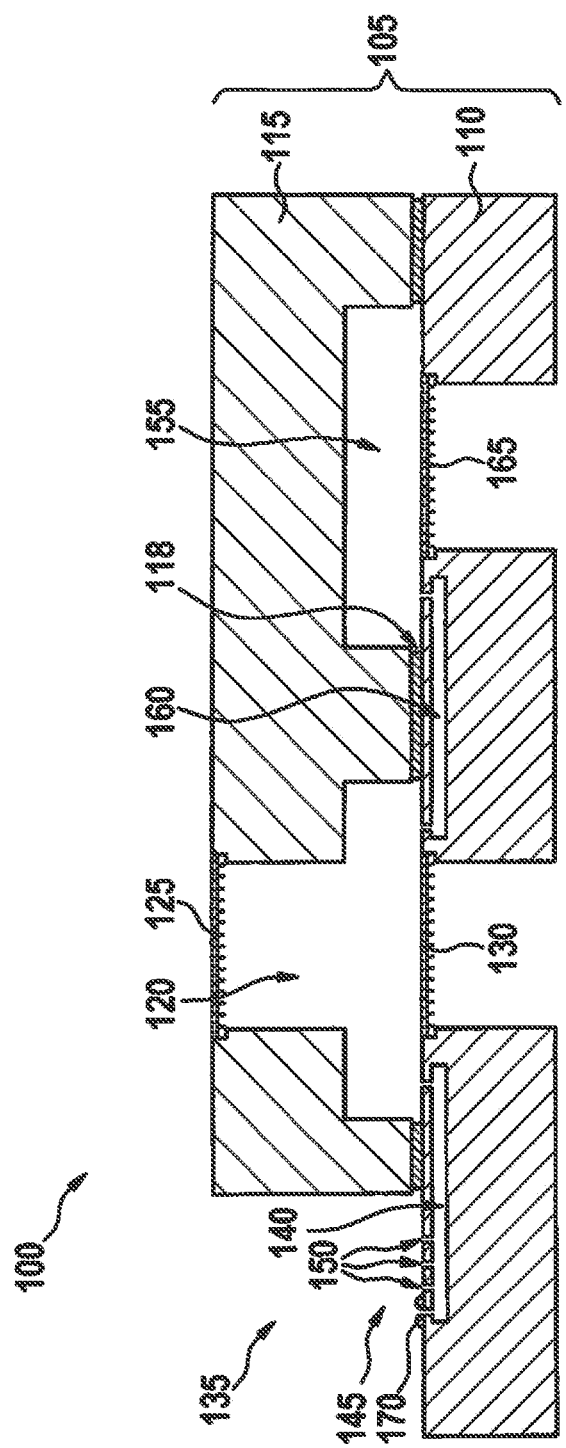
FIG. 1 shows a section through a semiconductor sensor.

FIG. 1 shows a semiconductor sensor 100 that includes a substrate 105, which may be silicon. In the specific embodiment shown, substrate 105 exists in the form of a lower carrier material 110 and an upper carrier material 115, which are combined on a horizontal separation plane in a sandwich-like manner. A bond 118 between carrier materials 110 and 115 may be formed from glass for example.

Semiconductor sensor 100 includes a first cavity 120, which is at least partially bounded by a pump diaphragm 125 and a first measuring diaphragm 130. The remainder is enclosed by substrate 105. A first fluid connection 135 comprising one or multiple diffusion channels 140 leads into the first cavity 120. Diffusion channel 140 may be embedded in substrate 105 of one of the carrier materials 110, 115 and leads from first cavity 120 to an inlet area 145, where multiple openings 150 of the diffusion channel 140 are situated. As will be shown later, it is alternatively also possible to provide multiple diffusion channels 140, which respectively have at least one opening 150 in inlet area 145.

In the specific embodiment shown, semiconductor sensor 100 is additionally configured to determine a nitrogen oxide concentration of a gas. An optional second cavity 155 is provided for this purpose, which is connected via an associated second fluid connection 160 to first cavity 120.

Semiconductor sensor 100 is configured to be adjusted after it has been manufactured, that is, when it is already operational, in that one or several of openings 150 are subsequently closed. The closure may occur in particular by way of laser light, material in the area of opening 150 melting in the process and depositing into opening 150, closing the latter hermetically when cooling. For this purpose, a material 170 may be situated in the area of an opening 150 on the substrate 105. Material 170 is chosen in such a way that it absorbs laser light of a predetermined wavelength to a greater degree than does substrate 105. In particular, material 170 may include silicon nitride, the utilized laser light being in the infrared range. The silicon of substrate 105 is essentially transparent for infrared radiation, the silicon nitride of material 170, however, is much less so. During irradiation by laser light, material 170 and thereby also substrate 105 heat up in the area of opening 150.

In the specific embodiment shown, pump diaphragm 125 is developed on upper carrier material 115. In another specific embodiment, pump diaphragm 125 may also be developed on lower carrier material 110 such that all active structures of semiconductor sensor 100 are situated in the same carrier material 110. In yet another specific embodiment, it is also possible for a diffusion channel 140 to run through one of measuring diaphragms 125, 130.

Figure 2:
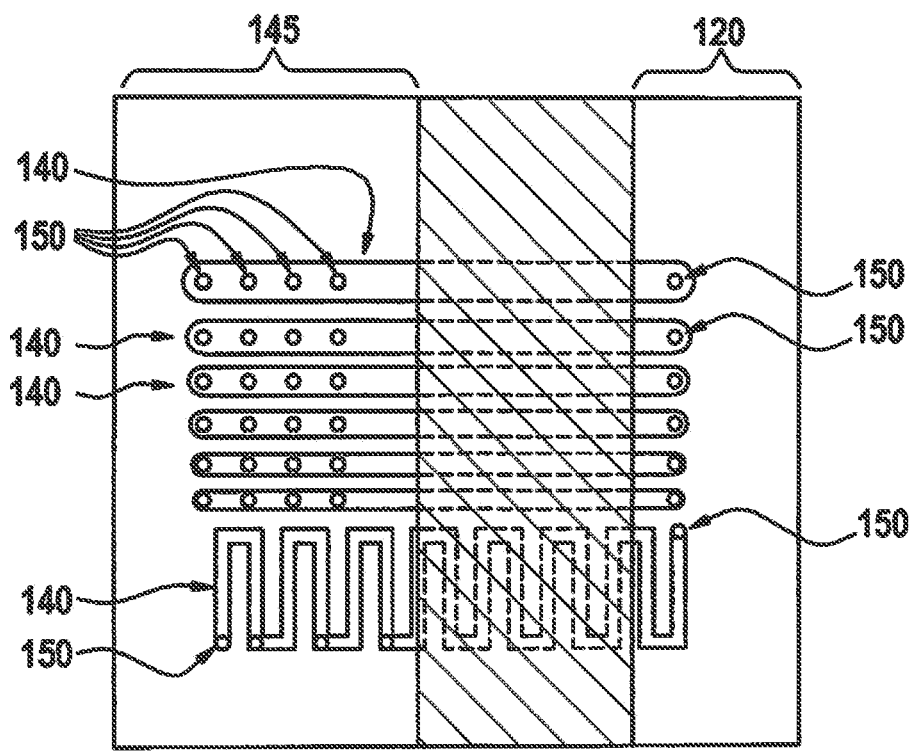
FIG. 2 shows a plan view of a section of the sensor from FIG. 1.

FIG. 2 shows a plan view on a section of sensor 100 from FIG. 1 in the area of the first fluid connection 135. Inlet area 145 may be seen in the left area of the illustration, while a part of the first cavity 120 may be seen in the right area. In between there is a section in which the upper carrier material 115 lies on the first fluid connection 135.

By selectively closing openings 150, it is possible to form the first fluid connection 135 from one or multiple diffusion channels 140, whose fluid properties may be adapted to the individual semiconductor sensor 100.

Figure 3:
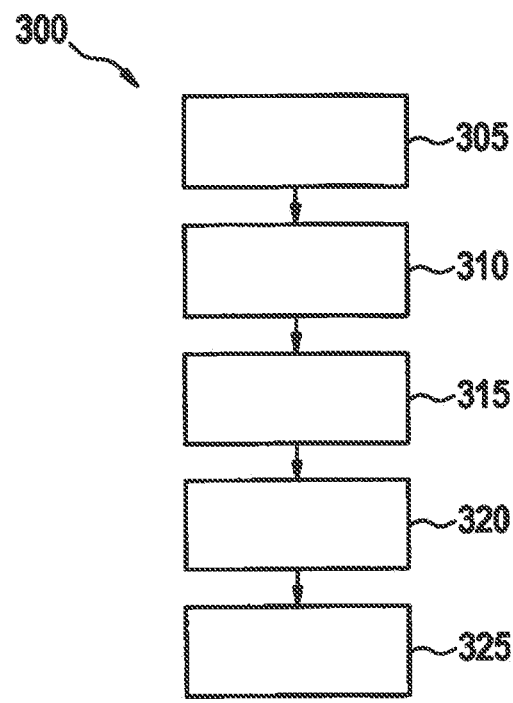
FIG. 3 shows a flow chart of a method for calibrating a semiconductor sensor.

FIG. 3 shows a flow chart of a method 300 for adjusting a semiconductor sensor 100 of FIG. 1 or 2. In a first step 305, semiconductor sensor 100 is provided. In a subsequent step 310, a gas having a known composition is provided in inlet area 145. The gas may have in particular a predetermined residual oxygen content that is to be determined using semiconductor sensor 100. In another specific embodiment, the gas may also have a predetermined concentration of nitrogen oxide ($NO_x$), which is to be determined using the semiconductor sensor 100 in the expanded specific embodiment shown in FIG. 1 including the second measuring diaphragm 165.

In another step 315, pump diaphragm 125 is controlled in such a way that a predetermined tension is established on first measuring diaphragm 130. Measuring diaphragm 130 may be constructed after the model of a Nernst cell, it being possible for the voltage to be 0.45 V.

In a step 320, the pump current is determined by pump diaphragm 125. The pump current gives an indication of the residual oxygen concentration in the gas present in inlet area 145. In order to establish a predetermined correlation between the pump current and the residual oxygen content of the gas, it is possible to close, in a step 325, one or multiple openings 150 of one or multiple diffusion channels 140, which may be done using a laser, in particular an infrared laser. If necessary, steps 315 through 325 may be iterated several times until the desired correlation is set.

In another specific embodiment, the second fluid connection 160 may also be calibrated in a similar manner.

Steps 315 and 320 are usually performed by a measuring system in order to perform a measurement on a gas using a semiconductor sensor 100. The measuring system may be in particular part of a control unit for controlling an internal combustion engine whose exhaust gas is analyzed by semiconductor sensor 100.

What is claimed is:

1. A semiconductor sensor, comprising:
a cavity;
a fluid connection between the cavity and an inlet area;
a pump diaphragm, which bounds the cavity; and
a measuring diaphragm, which bounds the cavity;
wherein the connection includes a diffusion channel having multiple openings in the inlet area or multiple diffusion channels having respectively one opening in the inlet area, and it is possible to close at least one of the openings using laser light to influence an effective length or an effective cross section of the fluid connection, and
wherein a material is provided in an area of at least one of the openings which absorbs infrared radiation to a greater degree than the fluid connection such that the material may be molten by an infrared laser to close the at least one of the openings.

2. The semiconductor sensor of claim 1, wherein the fluid connection and the cavity are configured in a semiconductor material.

3. The semiconductor sensor of claim 2, wherein the material that is provided in the area of the at least one of the openings absorbs infrared radiation to a greater degree than does the semiconductor material such that the material may be molten by an infrared laser to close the at least one of the openings.

4. The semiconductor sensor of claim 1, wherein the fluid connection includes the multiple diffusion channels, and the multiple diffusion channels have different effective cross sections.

5. The semiconductor sensor of claim 1, wherein the diffusion channel or at least one of the multiple diffusion channels runs in a meander form.

6. The semiconductor sensor of claim 1, wherein the cavity is configured between a first and a second semiconductor substrate, which are connected to each other.

7. The semiconductor sensor of claim 1, wherein there is a second cavity, which is connected via a second fluid connection to the first cavity and is bounded by a second measuring diaphragm.

8. A method for producing a semiconductor sensor, the method comprising:
 providing a semiconductor sensor, including:
  a cavity;
  a fluid connection between the cavity and an inlet area;
  a pump diaphragm, which bounds the cavity; and
  a measuring diaphragm, which bounds the cavity;
  wherein the connection includes a diffusion channel having multiple openings in the inlet area or multiple diffusion channels having respectively one opening in the inlet area, and it is possible to close at least one of the openings using laser light to influence an effective length or an effective cross section of the fluid connection;
 providing a gas having a known composition in the area of the inlet;
 controlling the pump diaphragm so that a predetermined tension is established on the measuring diaphragm; and
 closing at least one of the openings as a function of a pump current flowing through the pump diaphragm to establish a predetermined correlation between the pump current and the composition of the gas.

9. The method of claim 8, wherein providing the semiconductor sensor includes a unilateral hollowing out of a first semiconductor substrate and connecting the first semiconductor substrate to a second semiconductor substrate.

* * * * *